United States Patent [19]

Kleemann et al.

[11] 4,313,894

[45] Feb. 2, 1982

[54] PROCESS FOR THE PRODUCTION OF 3-CYANOPROPIONAMIDE

[75] Inventors: Axel Kleemann, Hanau; Wolfgang Leuchtenberger, Bruchkobel; Jürgen Martens, Alzenau; Horst Weigel, Rodenbach, all of Fed. Rep. of Germany

[73] Assignee: Degussa Aktiengesellschaft, Frankfurt, Fed. Rep. of Germany

[21] Appl. No.: 206,897

[22] Filed: Nov. 14, 1980

[30] Foreign Application Priority Data

Nov. 24, 1979 [DE] Fed. Rep. of Germany ....... 2947475

[51] Int. Cl.$^3$ .......................................... C07C 120/02
[52] U.S. Cl. ................................................. 260/465.4
[58] Field of Search ..................................... 260/465.4

[56] References Cited

U.S. PATENT DOCUMENTS

| | | | |
|---|---|---|---|
| 2,579,580 | 12/1951 | Houk et al. | 260/465.4 |
| 2,698,337 | 12/1954 | Heider | 260/465.4 |
| 2,810,742 | 10/1957 | Bortnick et al. | 260/465.4 |

FOREIGN PATENT DOCUMENTS

1132913 7/1962 Fed. Rep. of Germany .
782258 9/1957 United Kingdom .

OTHER PUBLICATIONS

Shenhau et al., J. Chem. Soc. (B), 1970, pp. 469–476.

*Primary Examiner*—Arthur P. Demers
*Attorney, Agent, or Firm*—Cushman, Darby & Cushman

[57] ABSTRACT

3-Cyanopropionamide is produced by adding hydrocyanic acid on acrylamide in the presence of an aprotic organic solvent and an alkali metal cyanide at a temperature between 20° and 150° C. 3-cyanopropionamide is an important intermediate product for the production of pyrrolidone or 4-aminobutyramide.

11 Claims, No Drawings

PROCESS FOR THE PRODUCTION OF 3-CYANOPROPIONAMIDE

BACKGROUND OF THE INVENTION 3-cyanopropionamide is an important intermediate product for the production of pyrrolidone or of 4-aminobutyramide and 4-aminobutyramide derivatives interesting as pharmaceuticals.

Known processes for the production of 3-cyanopropionamide start from succinodinitrile, which is partially saponified (see British Pat. No. 782,258 or German patent 1132913). Succinodinitrile itself is comparatively difficult to produce, and its partial hydrolysis over and above produces also unsatisfactory yields of 3-cyanopropionamide.

SUMMARY OF THE INVENTION

The invention is directed to a process for the production of 3-cyanopropionamide which is characterized by adding hydrocyanic acid on acrylamide in the presence of an aprotic organic solvent and an alkali metal cyanide at a temperature between 20° and 150° C.

Hydrocyanic acid (hydrogen cyanide) and acrylamide are readily available materials. The addition of hydrocyanic acid on the acrylamide proceeds surprisingly very smoothly and leads in high selectivity and very good yields to the 3-cyanopropionamide. Polymerization of the acrylamide takes place at all events to a very minor extent.

The hydrocyanic acid is suitably employed in a stoichiometric amount to the acrylamide, however, it can also be used in a slight excess.

The reaction takes place in the presence of an aprotic organic solvent. Especially preferred organic solvents are dimethyl formamide and dimethyl sulfoxide. Further suited organic solvents for example are diethyl formamide, dimethyl acetamide, N-methyl pyrrolidone, tetrahydrofuran, tetramethylene sulfone (sulfolan) and tetramethyl urea, as well as homologues of the named compounds with up to a total of 8 carbon atoms in the molecule, e.g. N,N-dimethyl-N',N'-diethyl urea, dipropyl acetamide. The amount of solvent is not critical, however, it should suitably be so measured that at the selected reaction temperature the acrylamide employed as well as the 3-cyanopropionamide formed are present in dissolved form.

The process of the invention furthermore requires the presence of an alkali metal cyanide as catalyst. Preferably sodium or potassium cyanide is used. The amount of catalyst also is not critical. For obtaining short reaction times, however, it is advantageous to employ the catalyst in an amount of 0.1 to 50, preferably from 5 to 20, weight percent, based on the amount of hydrocyanic acid employed.

The reaction takes place at a temperature between 20° and 150° C., preferably between 70° and 120° C. The pressure has no ascertainable influence on the speed of reaction and the composition of the reaction mixture after ending the reaction.

The process of the invention can be carried out in such manner that a suspension of the catalyst is present in a part of the solvent and a solution of the acrylamide and the hydrocyanic acid in the residual part of the solvent is fed in. However, just as well there can also be present a solution of the acrylamide in which the catalyst is suspended and the hydrocyanic acid led in. To recover the 3-cyanopropionamide formed, after complete reaction, the solution is concentrated and treated with a precipitating agent, for example toluene, whereupon 3-cyanopropionamide crystallizes out.

Unless otherwise indicated all parts and percentages are by weight.

The process can comprise, consist essentially of or consist of the stated steps with the indicated materials.

The invention will be explained in connection with the following examples:

EXAMPLE 1

There were slowly dropped into a suspension of 2 grams of potassium cyanide in 75 ml of dimethyl formamide at a temperature of 90° to 110° C. a solution of 71.08 grams (1 mole) of acrylamide and 27 grams (1 mole) of hydrocyanic acid in an additional 75 ml of dimethyl formamide. After a further reaction time of about 5 minutes, there were distilled 100 ml of dimethyl formamide in a water jet vacuum. The still warm distillation residue was stirred with 150 ml of toluene. Thereby the 3-cyanopropionamide formed crystallized out. After filtering off and drying at 60° to 70° C. this was determined to be 89.1 grams (91% of theory). Melting point: 90° to 93° C., after recrystallization from ethyl acetate: 93° to 95° C.

| $C_4H_6N_2$ Molecular Weight (98.11) | C | H | N |
|---|---|---|---|
| | 48.97% | 6.16% | 28.56% |
| | 48.97% | 6.06% | 28.32% |

EXAMPLE 2

Example 1 was repeated with the sole difference that in place of potassium cyanide there were used 2 grams of sodium cyanide. Yield: 89% of theory. Melting Point: 90° to 93° C. (recrystallized from isopropanol).

EXAMPLE 3

Example 1 was repeated with the sole difference that in place of dimethyl formamide there was used the same volume amount of dimethyl sulfoxide. Yield: 88% of theory. Melting Point: 89° to 92° C. (recrystallized from n-butanol).

EXAMPLE 4

Example 1 was repeated with the difference that in place of potassium cyanide there was used 2 grams of sodium cyanide and in place of the dimethyl formamide there was used the same volume amount of dimethyl sulfoxide. Yield: 89% of theory. Melting Point: 89° to 92° C.

EXAMPLE 5

There were suspended 2 grams of potassium cyanide in a solution of 71.08 grams (1 mole) of acrylamide in 100 ml of dimethyl formamide. Then there were led in at 40° to 50° C. 27 grams (1 mole) of hydrocyanic acid. After the ending of the introduction of hydrocyanic acid the reaction mixture was held for one hour at a temperature between 70° and 100° C. The dimethyl formamide was distilled off to reduce the volume in half and the residue stirred with 150 ml of toluene. There were obtained 91.1 grams of 3-cyanopropionamide (93% of theory) having a Melting Point of 93° to 95° C.

EXAMPLE 6

Example 5 was repeated with the sole difference that in place of potassium cyanide there were used 2 grams of sodium cyanide. Yield: 89% of theory. Melting Point: 90° to 93° C.

The entire disclosure of German priority application No. P 2947475.7-42 is hereby incorporated by reference.

What is claimed is:

1. A process for the production of 3-cyanopropionamide comprising reacting hydrocyanic acid with acrylamide at a temperature between 20° and 150° C. in the presence of an aprotic organic solvent and an alkali metal cyanide.

2. The process of claim 1 wherein the aprotic organic solvent is dimethyl formamide or dimethyl sulfoxide.

3. The process of claim 2 wherein the alkali metal cyanide is sodium or potassium cyanide.

4. The process of claim 1 wherein the alkali metal cyanide is sodium or potassium cyanide.

5. The process of claim 4 wherein the reaction is carried out at 70° to 120° C.

6. The process of claim 3 wherein the reaction is carried out at 70° to 120° C.

7. The process of claim 2 wherein the reaction is carried out at 70° to 120° C.

8. The process of claim 6 wherein the alkali metal cyanide is used in an amount of 0.1 to 50 weight percent based on the hydrocyanic acid employed.

9. The process of claim 4 wherein the alkali metal cyanide is sodium or potassium cyanide.

10. The process of claim 2 wherein the aprotic organic solvent is dimethylformamide.

11. The process of claim 2 wherein the aprotic organic solvent is dimethylsulfoxide.

* * * * *